(12) United States Patent
Bauman et al.

(10) Patent No.: US 7,935,730 B2
(45) Date of Patent: *May 3, 2011

(54) METHOD OF ENHANCING REPRODUCTIVE FUNCTION OF MAMMALS BY FEEDING OF CONJUGATED LINOLEIC ACIDS

(75) Inventors: Dale E. Bauman, Ithaca, NY (US); Euridice Castaneda-Gutierrez, Ithaca, NY (US); Walter R. Butler, Freeville, NY (US); Michael de Veth, Speyer (DE); Angelika-Maria Pfeiffer, Lambrecht (DE)

(73) Assignees: Cornell Research Foundation, Inc., Ithaca, NY (US); BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/424,635

(22) Filed: Apr. 16, 2009

(65) Prior Publication Data

US 2009/0203788 A1 Aug. 13, 2009

Related U.S. Application Data

(63) Continuation of application No. 11/353,887, filed on Feb. 14, 2006, now Pat. No. 7,531,574.

(51) Int. Cl.
*A01N 37/00* (2006.01)
(52) U.S. Cl. .................................................. 514/560
(58) Field of Classification Search .................. 514/560
See application file for complete search history.

(56) References Cited

U.S. PATENT DOCUMENTS

| 6,015,833 | A | 1/2000 | Saebo et al. |
| 6,288,114 | B1 | 9/2001 | Bauman et al. |
| 7,531,574 | B2 * | 5/2009 | Bauman et al. ............... 514/560 |

FOREIGN PATENT DOCUMENTS

| WO | 9966877 A2 | 12/1999 |
| WO | 02054886 A1 | 7/2002 |
| WO | WO02054886 | * 7/2002 |

OTHER PUBLICATIONS

Wade et al.; Control of fertility by metabolic cues; American Physiological Society, 1996, 270 (Endocrinol. Metab. 33); pp. E-1-E19.
Bernal-Santos et al.; Production Responses of Dairy Cows to Dietary Supplementation With Conjugated Linoleic Acid (CLA) During the Transition Period and Early Lactation; J. Dairy Sci., 2003, vol. 86; pp. 3218-3228.
De Veth et al.; Comparison of Calcium Salts and Formaldehyde-Protected Conjugated Linoleic Acid in Inducing Milk Fat Depression; J. Dairy Sci., 2005, vol. 88; pp. 1685-1693.
Castaneda-Gutierrez et al.; Dietary Supplements of Two Doses of Calcium Salts of Conjugated Linoleic Acid During the Transition Period and Early Lactation; J. Dairy Sci., 2005, vol. 88; pp. 1078-1089.
Perfield II et al.; Effects of Amide-Protected and Lipid-Encapsulated Conjugated Linoleic Acid (CLA) Supplements on Milk Fat Synthesis; J. Dairy Sci., 2004, vol. 87; pp. 3010-3016.

(Continued)

*Primary Examiner* — Deborah D Carr
(74) *Attorney, Agent, or Firm* — Hodgson Russ LLP

(57) ABSTRACT

This invention provides methods for improving reproductive performance of lactating dairy cows and other mammals. The method in the case of cows comprises feeding to the cows, a composition comprising conjugated linoleic acids (CLAs), cis-9, trans-11 and trans-10, cis-12. When these CLAs are fed daily to dairy cows starting at or prior to calving, and continued after parturition, an improvement in reproductive performance is observed.

10 Claims, 2 Drawing Sheets

OTHER PUBLICATIONS

Butler; Energy Balance Relationships With Follicular Development, Ovulation and Fertility in Postpartum Dairy Cows; Livestock Production Science, 2003, vol. 83; pp. 211-218.

Pariza et al.; The Biologically Active Isomers of Conjugated Linoleic Acid; Progress in Lipid Research, 2001, vol. 40; pp. 283-298.

Darwash et al.; A Protocol for Initiating Oestrus and Ovulation Early Post Partum in Dairy Cows; Animal Science, 2001, vol. 72; pp. 539-546.

Moore et al.; Increasing Amounts of Conjugated Linoleic Acid (CLA)Progressively Reduces Milk Fat Synthesis Immediately Postpartum; J. Dairy Sci., 2004, vol. 87; pp. 1886-1895.

Butler; Nutritional Effects on Resumption of Ovarian Cyclicity and Conception Rate in Postpartum Dairy Cows; Fertility in the High-Producing Dairy Cow, Occasional Publication No. 26—British Society of Animal Science ; pp. 133-145.

* cited by examiner

METHOD OF ENHANCING REPRODUCTIVE FUNCTION OF MAMMALS BY FEEDING OF CONJUGATED LINOLEIC ACIDS

This application is a continuation of U.S. application Ser. No. 11/353,887, filed on Feb. 14, 2006 now U.S. Pat. No. 7,531,574, the disclosure of which is incorporated herein by reference.

FIELD OF THE INVENTION

The present invention relates generally to the field of fertility of Mammals and more particularly provides compositions and methods for improving the fertility of lactating mammals including cattle.

BACKGROUND OF THE INVENTION

Poor fertility in cattle is estimated to cost $1 billion annually in the US. It is useful for farmers to synchronize the estrus of animals such as cattle (both dairy and beef) sheep, goats, horses, or the like where artificial insemination is practiced. By way of example, dairy cows must be impregnated once a year to maintain a lactation cycle in which milk is produced for ten months at a time with two month rest periods in between during which the cow is dry. Given the gestation period of a dairy cow, the objective is to impregnate the cow within 83 days after calving. The efficient management of a dairy herd thus requires that the cows be maintained at the peak of fertility to ensure re-impregnation within 83 days.

Accordingly, cattle producers and dairy scientists are continuously searching for nutritional supplements that promote dairy cow fertility. Fish oil fatty acids have become the focus of numerous research programs that seek to capitalize on their nutritional and physiological properties. WO 99/66877 to Amir et al. discloses the use of omega-3 fatty acids of fish oil origin to increase fertility in animals including cattle. Among the omega-3 fatty acids disclosed are eicosapentaenoic acid (EPA) and docosahexaenoic acid (DHA). WO 02/054886 to Lanna et al. provides for improved reproductive function in cows which were fed one daily dose of 150 g/day of calcium salts containing 70% fatty acids. Conjugated linoleic acid (CLA) isomers make up 60% of the fatty acids contained within the calcium salt formulation. Of the total CLA isomers approximately 24% was c/t 9, 11; 35% was c/t 10, 12; 15% was c/t 8, 10; 17% was t11, t13 and the remaining 9% was others. Knowing the concentrations of the individual isomers, a calculation of the amounts of cis-9, trans-11 and trans-10, cis-12 indicates that the dose used in this reference was about 15 g of cis-9, trans-11 and 22 g trans-10, cis-12 per day. Because the composition used in this reference contained significant amounts of several isomers, the effects could not be attributed to specific isomers. Additionally, because only a single concentration was used, there was no determination of a useful dosage for improvement of reproductive function. Further, the inventors describe how an improvement in energy balance allowed for the better reproduction. It is well known for all mammals that reproductive performance is compromised if nutrient intake is inadequate and this can be overcome by improving energy balance (Wade et al., 1996, Am. J. Physiol. 270:E1-E19).

Bernal-Santos et al. (2003, J. Dairy Sci. 86:3218-3228) disclose the administration of a single dose of 30 g/day of a CLA mixture comprising a mixture of various isomers. Of the total CLA isomers approximately 25.1% was c9, t11; 28.9% was t10, c12; 9.2% was t8, c10; 16.1% was c11, t13 and the remaining 20.7% was others. The authors concluded that no adverse effects were observed on conception and maintenance of pregnancy. However, the authors acknowledge that due to the limited number of animals in their study, they were unable to make any definitive conclusions regarding reproductive variables.

SUMMARY OF THE INVENTION

This invention provides compositions and method for enhancing the reproductive performance of mammals. The present invention is based on the observation that enhanced reproductive performance was observed in cows using compositions comprising specific isomers of CLA. Thus, the present invention provides a method of improving the reproductive function of female mammals comprising feeding to the female mammal a composition comprising two conjugated linoleic acids (CLA) isomers, cis-9, trans-11 and trans-10, cis-12.

In one embodiment, the composition comprises a CLA mixture with a high proportion of two isomers: cis-9, trans-11 and trans-10, cis-12. No other isomers of CLA are required to be present in this composition in any significant amount for the enhancement of reproductive function described herein. A dosage range was also observed for the enhancement in reproductive function. Above this dosage range, the enhancement effect is expected to diminish based on the observed trend. Accordingly, this invention also provides a method for enhancing the reproductive performance of mammals. The method comprises feeding to mammals, including mammals where artificial insemination is practiced, such as lactating cows, a composition comprising the two isomers of CLA, cis-9, trans-11 and trans-10, cis-12. Therefore, in one embodiment, the method of this invention comprises administering the CLA composition at a dose of 20 g/day and preferably 15 g/day or less of each of the two isomers. In another embodiment, the two isomers cis-9, trans-11 and trans-10, cis-12 make up at least 65%, preferably at least 70% of total CLAs, more preferably at least 80% and still more preferably at least 90% of the total CLAs. This method can be used for enhancing the reproductive function of mammals including cattle (beef and dairy), sheep, goats, horses, pigs, rabbits, dogs and humans.

DETAILED DESCRIPTION OF THE INVENTION

Figure 1:
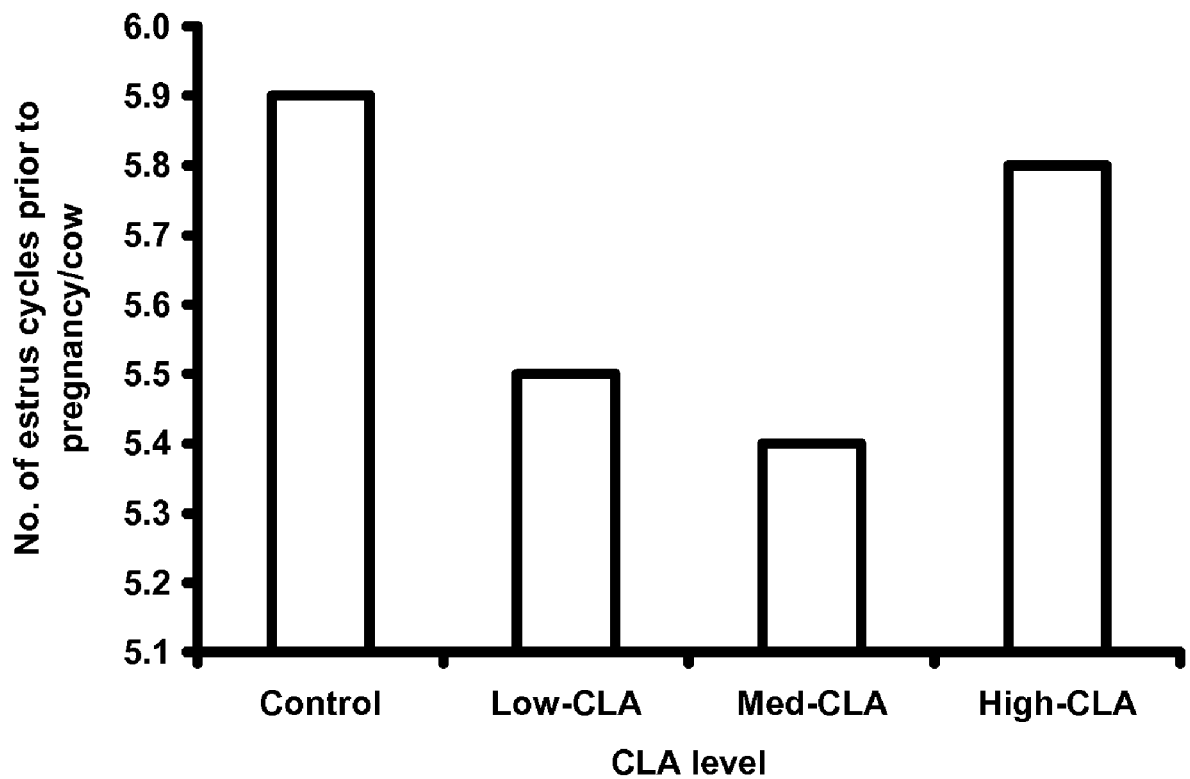
FIG. 1 is a graphic representation of the effect of feeding CLA isomers cis-9, trans-11 and trans-10, cis-12 to lactating cows on the number of ovulations.

The method of the present invention provides a method for improving the reproductive function of female mammals by administering conjugated linoleic acid isomers. Conjugated linoleic acid (CLA) isomers are a mixture of positional and geometric isomers of octadecadienoic (linoleic) acid with conjugated double bonds. There are 28 possible isomers of CLA. These include isomers having double bonds at 7 and 9, 8 and 10, 9 and 11, 10 and 12 or 11 and 13 position and isomers that have the double bond pairs with geometric configurations of cis-cis, trans-trans, cis-trans and trans-cis.

This invention is based on the observation that a mixture of CLA isomers comprising the two isomers, trans-10, cis-12 CLA and cis-9, trans-11 CLA within a particular range of dosage provides enhancement of reproductive function of dairy cows. Accordingly, in one embodiment, this invention provides a range of dosage of two CLA isomers which when fed to mammals improves their reproductive function. Above this range, the enhanced effects on reproductive function are diminished. During the first 6-8 weeks post-partum the nutrient intake of cows is less than their nutrient requirements. This is referred to as a negative energy balance and extensive research has established that technologies and practices that cause improvements in the energy balance of cows in early lactation result in improvements in reproductive performance (Butler, 2001, Animal Science Occasional Publication No. 26 (Vol. 1):133-145; Butler, 2003, Livest. Prod. Sci. 83:211-218; Darwash et al., 2001, Animal Science 72:539-546). However, at the concentrations useful in enhancement of reproductive performance, it was observed that there was no significant effect on net energy balance. Therefore, an improvement in reproductive performance with the feeding of CLA isomers as described herein is not dependent on an improvement in energy balance.

The identification of specific isomers for which a dose dependent enhancement in reproductive function is observed, is important because CLA isomers are known to sometimes have different or even opposite effects. For example, trans-10, cis-12 CLA causes reduction of milk and body fat, whereas cis-9, trans-11 CLA has no effect. Further, cis-9, trans-11 CLA is proposed to enhance feed efficiency and growth in young rodents but trans-10, cis-12 CLA does not (Pariza et al, 2001, Prog. Lipid Res. 40(4):283-298).

The present invention provides methods for improving the reproductive performance of mammals. In one embodiment, the compositions comprise primarily two CLA isomers cis-9, trans-11 and trans-10, cis-12 in amounts such that administration or feeding of the CLAs to cows will result in a daily dose of less than or equal to 20 g/day for each isomer. In one embodiment, the compositions provide a dose of less than or equal to 18 g/day and preferably less than or equal to 15 g/day for each isomer. In other embodiments, various concentrations of the two isomers can be used such that the dose of each is independently between 1 and 20 g/day. In another embodiment, the cis-9, trans-11 and the trans 10, cis-9 isomers can make up greater than 65%. For example, in different embodiments, the cis-9, trans-11 and the trans 10, cis-9 isomers can make up 70, 80 or 90% of the CLAs. In one embodiment, the combined percentage of 11, 13 isomers, the 8, 10 isomers and double trans isomers is less than one percent. In one embodiment, the ratio of the two isomers, cis-9, trans-11 and the trans 10, cis-9, is between 1:5 to 5:1. In another embodiment, the ratio is between 1:2 to 2:1 and in yet another embodiment, the ratio is approximately 1:1. The preparation of such compositions is described in U.S. Pat. No. 6,015,833, incorporated herein by reference. In one embodiment, the composition is fed to the cows such that a dosage of 1-15, preferably 2-14, more preferably 3-13, particularly preferably 4-12 and even more preferably 5-10 g/day of each isomer is administered. In a more preferred embodiment, the daily dose is between 6-14, preferably 7-13, more preferably 8-12 g/day for each isomer.

The method of the present invention comprises providing a composition comprising primarily of cis-9, trans-11, and trans-10, cis-12 isomers and feeding the CLA composition to mammals (including, but not limited to, dogs, horses, pigs, rabbits and humans), preferably ruminants like cows, sheep or goats, more preferably lactating ruminants like dairy cows or beef cows. The animals are fed feedstock containing the above described conjugated linoleic acids at concentrations such that upon feeding of the feedstock to the cows, the reproductive performance of the animals is increased preferably at concentrations between 6-14, preferably 7-13, more preferably 8-12 g/day for each isomer.

For human applications, the CLA isomers can be provided in a variety of forms. The dosage will depend upon the weight and metabolic rate of the individuals. Based on the guidance provided herein, those skilled in the art can determine the appropriate dosage. The administration may be oral wherein the CLA isomers are formulated with suitable carriers such as starch, sucrose or lactose in tablets, pills, dragees, capsules, solutions, liquids, slurries, suspensions and emulsions. CLA isomers may also be administered by other routes such as by intravenous, intramuscular, transdermal, subcutaneous, intraperitoneal, or mucosal routes. Such administration regimes can be found in Remington's Pharmaceutical Sciences (Maack Publishing Co., Easton, Pa.).

By improved reproductive function or an enhanced fertility is meant an improvement is observed in one or more of the following: interval between calving and first ovulation; improvement in maintenance of pregnancy; increased embryonic survival or the percentage of female mammals, preferably cows in a herd that become pregnant; period of time (interval) until the mammals get pregnant; decreased services per conception, and early embryo survival.

For ruminants, the CLA compositions can be delivered by infusing directly into the abomasum as a convenient experimental approach to avoid possible alterations by rumen bacterial fermentation. However, in commercial practice this is not feasible, so the dietary supplement of CLA has to be formulated in a manner so that it is protected to minimize its metabolism by rumen bacteria and can pass directly to the abomasum. Exemplary methods for rumen-protection of CLA to minimize its metabolism by rumen bacteria include, but are not limited to, encapsulation in a lipid-protein matrix or with water insoluble lipids; formaldehyde treatment; formation of calcium salts; and linkage by amide bonds.

Formaldehyde protection, encapsulates lipid in a matrix of protein and through cross-linkages are formed between the formaldehyde and protein which confer resistance to microbial attack in rumen (Scott and Cook, 1975, pp 510-523 in Digestion and Metabolism in the Ruminant. I. W. McDonald and A. C. I. Warner, ed. The University of New England Publishing Unit, Sydney, Australia). The mechanism whereby calcium salts provide "protection" is related to the inertness of the calcium-fatty acid complex on rumen digestion; it does not appear to be related to protection from rumen biohydrogenation. Microencapsulation is a lipid based protection method that either embeds the active ingredient in a lipid matrix or produces small spheres of the nutrient which are encapsulated (Wu and Papas, 1997, Advanced Drug Delivery Reviews 28:323-334).

A number of recent studies have shown that all four methods mentioned above provide protection for CLAs when fed to lactating dairy cows and were effective based on the absorption and incorporation of the CLA isomers into milk fat (Bernal-Santos et al., 2003, Moore et al., 2004, J. Dairy Sci. 87:1886-1895; Perfield et al., 2004, J. Dairy Sci. 87:3010-3016, and de Veth et al., 2005, J. Dairy Sci. 88:1685-1693). Determination of level of protection using other methods can be done by routine methods and is well within the purview of those skilled in the art.

A commercially available type of rumen protection used for the supplement is lipid encapsulated CLA (BASF, Ludwigshafen, Germany; Balchem Encapsulates, USA). The present method can be used for enhancing reproductive performance of mammals including ruminants such as cows (including beef and dairy cattle), goat and sheep. While specific examples and dosages are presented herein with respect to cows, it will be appreciated by those skilled in the art, that based on the information provided herein, appropriate dosages for other ruminants as well as other mammals can be easily determined.

The feeding of CLA composition to mammals can begin prior to calving or at calving and can be continued for period of at least 2 weeks. In further embodiments, the feeding can continue for a period between 50 to 75, for a period of 76 to 100, for a period of 101 to 125, for a period of 126 to 150, or for a period of 151 to 200 days after calving. The treatment can also be continued beyond 200 days after calving. For example, the feeding of CLA can begin about 2 weeks prior to calving and can end about 2 weeks after calving, or about 50 days after calving, or about 90 days after calving, or about 200 days after calving. Although it is preferred that the dairy cows are fed the composition daily such that a dosage of 1-20 g/day and more preferably between 1-18 g/day and even more preferably 1-15 g/day of each of cis-9, trans-11 CLA and trans-10, cis-12 CLA is delivered to the animal, those skilled in the art will recognize that the feeding schedule includes instances wherein the composition is inadvertently or intentionally (such as because of a temporary medical condition) deleted from the daily diet during a short period of time during the administration period. It is preferable that such break in CLA administration does not exceed 14 consecutive days and more preferable that it does not exceed 7 consecutive days.

While the present invention is illustrated by way of the following examples, the examples are meant only to illustrate particular embodiments of the present invention and are not meant to be limiting in any way.

Example 1

This example describes the effect of a CLA isomer mixture administered at two doses on the reproductive performance of cows. All procedures involving animals were approved by the Cornell University Institutional Animal Care and Use Committee. Multiparous Holstein cows (n=48) from the Cornell University Dairy Teaching and Research facility were blocked by parity and by 305-day mature equivalent milk production in the previous lactation and assigned in a randomized complete blocked design to one of the following 3 dietary treatments: 1) control, consisting of 271 g/d of Ca salts of palm fatty acid distillate (EnerGII; Bioproducts Inc., Fairlawn, Ohio); 2) conjugated linoleic acid dose 1 (CLA-1), consisting of 147 g/day of Ca salts of mixed isomers of CLA (Bioproducts Inc.) and 136 g/day of Ca salts of palm fatty acid distillate; or 3) conjugated linoleic acid dose 2 (CLA-2) consisting of 295 g/day of Ca salts of mixed isomers of CLA. The weight of the lactating Holstein cows is generally between 500 to 700 kg.

Supplements of Ca salts of palm fatty acid distillate and Ca salts of CLA contained 85 and 78% fat, respectively. The 3 supplements provided the same intake of fat (230 g/day) and were top-dressed once daily on the total mixed rations (TMR) from 21 day before expected day of calving to 63 days in milk (DIM). The CLA-1 and CLA-2 treatments provided 31.6 and 63.2 g/day of CLA isomers, respectively. The 4 predominant CLA isomers in the supplements were trans-8, cis-10 (21.2%), cis-9, trans-11 (21.8%), trans-10, cis-12 (29.0%), and cis-11, trans-13 (28.0%). Thus, CLA-1 provided 6.8 g/day of cis-9, trans-11 CLA and 9.2 g/day of trans-10, cis-12 CLA whereas CLA-2 provided twice these amounts. The predominant fatty acids in the Ca salts of palm fatty acid distillate were palmitic (42.6%), oleic (40.6%), and linoleic acids (10.1%).

Cows were housed in tie stalls and fed at ad libitum intake to allow about 10% orts. Individual feed intake was recorded from 14 days before the expected date of calving to 63 DIM. During the post-treatment period (64 to 126 DIM), cows were combined in groups independent of treatment and fed a common diet. Water and mineral blocks were available throughout the study. Body weight and body condition score (BCS) (5-point system; Wildman et al., 1982, J. Dairy Sci., 65:495-501) were recorded weekly after the morning milking. After calving, cows were milked 3×/day, and milk weight was recorded. A milk sample from each milking was taken 1 day/week, and a composite was formed based on proportion of daily yield. Composite milk samples were stored at 4° C. with a preservative (bronopol tablet; D& F Control System, San Ramon, Calif.) until analyzed for fat, true protein, and lactose (Dairy One Cooperative Inc., Ithaca N.Y.) Blood samples were taken at 10 and 5 days prepartum, 3×/week during the first 11 wk of lactation, and once weekly from week 12 to 18 postpartum. Blood (10 mL) was obtained via coccygeal venipuncture and was collected in vacuum tubes (Becton Dickinson Vacutainer Systems, Franklin Lakes, N.J.) containing sodium heparin (100 U/mL of blood). Plasma was harvested within 20 min after collection by centrifugation (2800×g for 15 min at 4° C.) and stored at −20° C. until metabolite and hormone analysis. Estrus was synchronized with an intramuscular injection of 100 mg of GnRH analogue (Cystorelin; Abbott Laboratories, North Chicago, Ill.) at d 70±3 (mean±SD) postpartum; 7 days later, cows received an injection of 30 mg of PGF2α analogue (Lutalyse; Pharmacia & Upjohn, Kalamazoo, Mich.); 48 hours later, they received an injection of 100 mg of GnRH and were inseminated 4 to 8 h later. Pregnancy was diagnosed by rectal palpation at 42 days after insemination. After the experimental period (>126 DIM), nonpregnant cows were resynchronized or inseminated when estrus was visually detected; if conception occurred before 185 d postpartum, this was recorded and used for statistical analysis.

A total of 46 of the 48 cows completed the treatment period. One cow from each CLA treatment group was excluded (all analysis) because of health reasons (chronic laminitis). In addition, 2 cows in the CLA-1 treatment group completed the treatment period but not the post-treatment period because of chronic laminitis and death caused by a respiratory problem.

Net energy balance was computed for each cow in the experiment according to the equations published by the National Research Council (NRC, 2001, in Nutrient Requirements of Dairy Cattle, $7^{th}$ Revised Ed., National Academy Press, Washington, D.C.). The estimate is calculated from the difference between total energy intake (dry matter intake multiplied by the net energy value of the diet) minus the sum of energy requirements for the cow's maintenance and her milk production. The energy requirement for maintenance is based on the cow's size (body weight), and the energy requirement for milk production is based on the daily milk yield and the composition of the milk (fat, protein and lactose). There was no difference in net energy balance among the treatments (P value=0.54)

Figure 2:
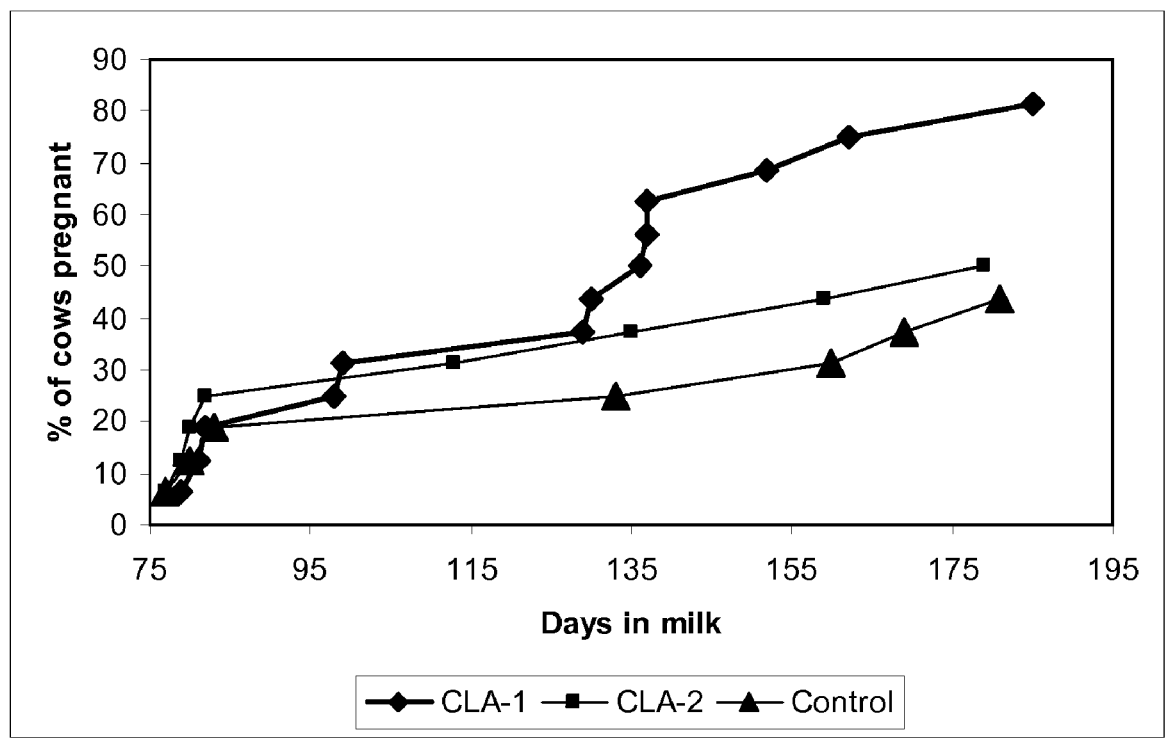
FIG. 2 is a graphic representation of the survival analysis of the maintenance of pregnancy for cows fed with two CLA concentrations as compared to control.

Plasma concentrations of progesterone and estradiol were determined by radioimmunoassay (Elrod and Butler, 1993, J. Animal Sci. 71:694-701; Beam and Butler, 1997, Biol. Reprod. 56: 133-142). Progesterone was analyzed on the plasma samples obtained 3×/week during the first 11 weeks of lactation, whereas estradiol was analyzed on the plasma samples from the first 3 week postpartum. Ovulation was determined based on temporal pattern and concentration of plasma progesterone according to the criteria described by Butler et al. (1981). The results of the study are shown in Table 1. The mean and median days to first ovulation were lower for cows supplemented with CLA-1 (P=0.05). The proportion of cows pregnant before 185 days differed among treatments (P=0.07), with the highest value observed for the CLA-1 group. The percentage of cows pregnant before 126 DIM of the 2 CLA groups was similar (31.1 and 33.3%) and numerically greater than the control group (18.7%). As shown in the survival analysis (FIG. 2) the CLA-1 dose dramatically increased the percent cows pregnant in the interval beyond 135 days postpartum. These results suggest that the CLA-1 supplement reduced embryonic mortality thereby resulting in a marked enhancement of pregnancy survival rates.

TABLE 1

Reproductive performance data for Example 1.

| | Treatment[1] | | | |
|---|---|---|---|---|
| Variable | Control | CLA-1 | CLA-2 | P-value |
| Days to first ovulation | | | | |
| Mean | 32.6 | 27.3 | 41.4 | 0.05 |
| Median | 34.0[ab] | 21.5[b] | 41.3[a] | 0.05 |
| Days to pregnancy | | | | |
| Mean[2] | 160 | 135 | 151 | 0.81 |
| Median[3] | 146 | 137 | 124 | 0.54 |
| Ovulation before synchronization[4,5] | 1.6 | 1.7 | 1.5 | 0.63 |
| Cows pregnant before 126 DIM, % | 18.7 | 31.3 | 33.3 | 0.63 |
| Cows pregnant before 185 DIM, % | 43.7 | 81.3 | 53.3 | 0.07 |
| Services per conception | 2.5 | 2.2 | 2.0 | 0.57 |
| Proportion of cows with estrogen active follicles in the first 21 DIM[6], % | 73.3 | 57.1 | 60.0 | 0.63 |
| Proportion of cows with ovulation in the first 21 DIM, % | 18.8 | 46.7 | 7.1 | 0.63 |
| Progesterone peak at first ovulation, ng/dl | 7.7 | 6.5 | 6.8 | 0.58 |

[1]Cows received a dietary fat supplement consisting of Ca salts of palm fatty acid distillate (271 g/day) (control treatment), Ca salts of a mixture of conjugated linoleic acid isomers (147 g/day containing 32 g/day CLA isomers; 9 g/day of CLA trans-10, cis-12) plus palm fatty acid distillate (136 g/day) (CLA-1), or Ca salts of a mixture of conjugated linoleic acid isomers (295 g/day containing 63 g/day CLA isomers; 18 g/d of CLA trans-10, cis-12) (CLA-2).
[2]Pregnancies recorded before 185 days postpartum.
[3]Cows were removed if they were not pregnant before 185 days postpartum (3 from CLA-1 group, 5 from CLA-2 group and 8 from control group).
[4]Synchronization occurred at 67 days postpartum.
[5]Ovulation determined when plasma progesterone levels were above 0.5 ng/ml for at least five consecutive samples, and exceeded 2 ng/ml for at least two successive samples.
[6]Follicular activity during the first 21 day postpartum was assumed when estrogen level >2 pg/ml.

A similar effect was seen when the cows were fed with a composition in which the two isomers—cis-9, trans-11 CLA and trans-10, cis-12 CLA made up more than 90% of the total CLA.

Example 2

This example describes the effect of two CLA isomers on reproductive function and establishes a cutoff dose for observing enhanced reproductive function. By using different doses of the two isomers, a dose dependent effect on reproductive function was observed. The effects of rumen protected CLA on reproductive performance was studied using 4 doses of rumen-protected CLA supplement (BASF, Ludwigshafen, Germany). The type of rumen protection used for the supplement was lipid-encapsulation commercially obtained from Balchem Encapsulates, New Hampton, N.Y. The supplement contained 20% CLA isomers. Of the total CLA isomers, 50% was cis-9,trans-11 and 50% was trans-10, cis-12 CLA and the four treatment levels provided 0, 5, 10 and 15 g/day of each CLA isomer. The supplement was fed once daily by top-dressing over the basal diet (fed ad-libitum), with cows receiving an additional concentrate supplement. The experiment started at calving and dietary supplements of CLA continued until all cows were 91 days into lactation. Animals were also monitored after the treatment period so that effects of CLA treatment on reproductive indices could be fully determined.

The net energy balance and reproductive performance were estimated as described in Example 1. No change in net energy balance was seen as dose increased from 0 to 15 g/d of each isomer (P value=0.20). Results demonstrate that CLA treatment improved overall conception rate (P=0.03) and reduced the median number of days until pregnancy (P=0.07) (Table 1). The effect seen was a quadratic response to dose. The quadratic relationship indicates that as the dose of CLA is increased, the reproductive performance improves, but as the dose is increased beyond a certain level the beneficial effects on reproductive performance are diminished. The quadratic relationship also shows that although for the high CLA sometimes the reproductive performance appears to be better than the control (numerically) that in fact the performance is diminished at this high dose. This enables the determination of a dose range for enhancement of reproductive performance whereby the greatest improvement in reproductive performance occurred at the low and medium doses (5 and 10 g/day of each CLA isomer). Additionally, there was a reduction in the number of services per conception (Table 2) and fewer ovulations per cow (recorded as number of estrus cycles prior to pregnancy; FIG. 1) at the low and medium dose levels, however, at the high treatment level (15 g/day of each CLA isomer) a trend toward reduction of the effect was seen. Similar to Example 1, the pattern of reproductive variables indicates that embryonic survival is improved with the low and medium doses of CLA.

TABLE 2

Reproductive performance of cows receiving four doses of CLA

| | Treatment | | | | |
|---|---|---|---|---|---|
| | Control | Low CLA | Med CLA | High CLA | P Quadratic |
| Services per conception | 2.1 | 1.7 | 1.5 | 2.0 | 0.25 |
| Days until pregnancy, median | 136 | 110 | 92 | 100 | 0.07 |
| Conception rate % | 64 | 87 | 100 | 80 | 0.03 |

These results show that a CLA supplement that is fed to provide cis-9, trans-11 and trans-10, cis-12 CLA doses between 5-15 g/day (of each isomer) will improve reproductive performance. At doses above this range (≧15 g/day of each isomer) the beneficial effects on reproductive performance may be reduced.

The foregoing description of the specific embodiments is for the purpose of illustration and is not to be construed as restrictive. From the teachings of the present invention, those skilled in the art will recognize that various modifications and changes may be made without departing from the spirit of the invention.

What is claimed is:

1. A method of improving the reproductive function of female mammals, the method comprising feeding the female mammals a composition comprising conjugated linoleic acids (CLAs), wherein the CLAs in the composition consist essentially of cis-9, trans-11 and trans-10, cis-12 CLA, in an amount such that reproductive function of the female mammals is improved but there is no effect on net energy balance, and wherein the mammal is selected from the group consisting of cows, sheep and goats.

2. The method of claim 1, wherein the cow is a beef cow or dairy cow.

3. The method of claim 2, wherein the cow is a dairy cow and is fed between 1 and 20 g grams/day of each CLA isomer.

4. The method of claim 3, wherein the dairy cow is feed between 1 and 15 grams/day of each CLA isomer.

5. The method of claim 4, wherein the dairy cow is fed between 3-13 g/day of each CLA isomer.

6. The method of claim 5, wherein the dairy cow is fed between 5-10 g/day of each CLA isomer.

7. The method of claim 1, wherein the improved reproductive function is selected from the group consisting of (a) shorter interval between parturition and first ovulation;
(b) increased maintenance of pregnancy;
(c) increased embryonic survival;
(d) increased likelihood of pregnancy;
(e) shorter time interval for cows to become pregnant; and
(f) decreased services per conception.

8. The method of claim 7, wherein the composition is fed daily to the beef cow or dairy cow at least for a period starting at calving and ending about 2 weeks after calving.

9. The method of claim 7, wherein the composition is fed daily to the beef cow or dairy cow at least for a period starting at calving continued for 50 to 100 days after calving.

10. The method of claim 7, wherein the composition is fed daily to the beef cow or dairy cow at least for a period starting at calving continued for 50 to 200 days after calving.

* * * * *